United States Patent [19]
Comyns et al.

[11] Patent Number: 4,687,871
[45] Date of Patent: Aug. 18, 1987

[54] PROCESS FOR THE RESOLUTION OF A RACEMATE

[75] Inventors: Alan E. Comyns, Chester; Gareth W. Morris, Spital Wirral; John P. Sankey, Great Sankey Warrington, all of England

[73] Assignee: Laporte Industries Limited, London, England

[21] Appl. No.: 796,002

[22] Filed: Nov. 7, 1985

[30] Foreign Application Priority Data

Nov. 17, 1984 [GB] United Kingdom ................ 8429121
Apr. 2, 1985 [GB] United Kingdom ................ 8508619

[51] Int. Cl.$^4$ ........................ C07F 1/08; C07C 51/15; C07C 147/00
[52] U.S. Cl. .................... 556/138; 568/27; 564/424
[58] Field of Search ............... 564/424; 556/138; 568/27

[56] References Cited

U.S. PATENT DOCUMENTS

| | | | |
|---|---|---|---|
| 2,946,821 | 7/1960 | Schenck et al. | 556/138 X |
| 3,038,904 | 6/1962 | Godfrey | 556/138 X |
| 3,054,746 | 9/1962 | Gaden, Jr. et al. | 556/138 X |
| 3,069,470 | 12/1962 | Fleck et al. | 564/424 |
| 3,419,619 | 12/1968 | Söder et al. | 568/27 |
| 4,371,721 | 2/1983 | Wu | 568/27 X |
| 4,467,126 | 8/1984 | Zinnen | 564/424 X |
| 4,480,128 | 10/1984 | Arpe et al. | 564/424 |
| 4,480,129 | 10/1984 | Priegnitz et al. | 564/424 |
| 4,554,380 | 11/1985 | Arpe et al. | 564/424 |

OTHER PUBLICATIONS

Chemical Abstracts, 76 104159u (1971).

*Primary Examiner*—Helen M. S. Sneed
*Attorney, Agent, or Firm*—Kane, Dalsimer, Kane, Sullivan and Kurucz

[57] ABSTRACT

A racemate may be resolved into its enantiomers by stereoselective adsorption on a crystalline molecular sieve having an assymetric crystal structure for example zeolite ZSM11. The resolution may be assisted by the presence of an enantiomer of a compound separable from that of the racemate either preadsorbed on the molecular sieve or included in a polar solvent solution of the racemate to be treated. Resolution of an alkyl aryl sulphoxide racemate is exemplified.

21 Claims, No Drawings

PROCESS FOR THE RESOLUTION OF A RACEMATE

BACKGROUND OF THE INVENTION

Field of the Invention

BRIEF DESCRIPTION OF THE PRIOR ART

This invention relates to the resolution of a racemate into its optically active enantiomers.

Many compounds which play significant roles in biological processes do so in their naturally occurring enantiomeric forms. Synthetic routes to these compounds often produce the racemate and require lengthy and expensive modification to produce separate enantiomers. As a result synthetic enantiomers for use in biochemical research or development, for example for the production of pharmaceuticals, or chemotherapeutic agents, vitamins or hormones, command market prices vastly in excess of those of the corresponding racemates.

One group of compounds to which the above described situation applies are the alkyl aryl sulphoxides, such as methyl paratoluene sulphoxide usable in one enantiomeric form in the synthesis of both maytansine, an antitumour and chemotherapeutic material, and vitamin E (alpha-tocopherol).

Attempts have been made to resolve racemates by stereoselective adsorption onto a solid surface. It has been suggested that optically asymmetrical crystal surfaces, such as that of d- or l-quartz, may be effective stereoselective adsorbents. Unequivocal affirmative results have apparently not been obtained, however, in view of the statement by Professor R. D. Gillard (Chemistry in Britain November 1984, pages 1022–1024) that rotational results, apparently showing stereospecific adsorption, may be spurious since they may readily be caused by processing techniques, particularly by inefficient filtration leaving ultramicroscopic particles suspended. At any rate, no practical process for the resolution of racemates based on the surface adsorption properties of optically active quartz or any other inorganic material has been described.

It is now realised, according to the invention, that certain crystalline molecular sieve materials are crystallographically assymetrical and also that this assymetry is reflected in the morphology of their internal pore structure so as to render them usable for the resolution of racemates into their constituent enantiomers. This property is hereafter called "chiral" activity.

SUMMARY OF THE INVENTION

According to the present invention there is therefore provided a process for the resolution of a racemate by stereoselective adsorption on a solid adsorbent characterised by the use of a crystalline molecular sieve material having an asymmetrical crystal structure as the adsorbent. Preferably the racemate is treated in the liquid or vapour form or as a solution of or containing an organic, particularly preferably a polar organic, solvent. According to one aspect of the invention the contact is conducted in the presence of a "distinct" enantiomer by which is meant an enantiomer of a compound chemically and/or physically distinct from and therefore separable from the racemic compound or its enantiomers.

By the term "molecular sieve" is meant a material containing pores of a size which will accept molecules below a certain size thereby enabling said molecules to be 'sieved' or separated from larger molecules. Typically in zeolite molecular sieves the pores are from about 2 Angstroms to about 20 Angstroms in diameter.

DETAILED DESCRIPTION OF THE PREFERRED EMBODIMENTS OF THE INVENTION

The molecular sieves preferred to use according to this invention are for example, but not exclusively, those based on three dimensional silica frameworks such as silicalite, or the aluminosilicates and other metallosilicates collectively referred to as "zeolites" or the aluminophospates. Due to their physical and chemical stability and their high internal surface area of specifically sized channels such materials have proved ideally suited to use in industrial adsorptive processes.

The molecular sieve material may also be derived by the removal of residual templates from aluminophosphate molecular sieves such as those described in U.S. Pat. No. 4,310,440 which have the general formula $Al_2O_3$ 1.0 $+/-$ 0.2 $P_2O_5$ and contain uniform pores having dimensions of from about 3 to about 10 Angstroms.

The molecular sieve material may also be derived by the removal of residual template from the so-called organosilicates described in U.S. Pat. No. 3,941,871 which are essentially silica framework materials containing less than a small proportion of alumina and a small proportion of template derived organic cations.

The molecular sieve material may also be selected from the silica polymorphs described in U.S. Pat. No. 4,073,865.

In crystallography it is recognised that there are 11 "enantiomorphous" and 4 "non-enantiomorphous" point groups in which crystal asymmetry can exist. These are summarised in Table I.

TABLE I

| | Point Groups | | | |
|---|---|---|---|---|
| System | Enantiomorphous | | Non-enantiomorphous | |
| Triclinic | 1 | | | |
| Monoclinic | 2 | | m | |
| Orthorhombic | 222 | | mm2 | |
| Tetragonal | 4 | 422 | 4 | 42m |
| Trigonal | 3 | 32 | | |
| Hexagonal | 6 | 622 | | |
| Cubic | 23 | 432 | | |

By utilising techniques known in the art of crystallography, for example as summarised in the book "Elementary Crystallography" by Martin J. Buerger, published by MIT Press 1963 in the chapter entitled "Practical determination of point group symmetry" and by x-ray powder diffraction and nuclear magnetic resonance studies crystalline molecular sieve materials such as zeolites may be allocated to their appropriate symmetry groups. Those which fall within the 15 point groups set out in Table I may be used in the practice of this invention. By way of example the point groups, and the appropriate space group within each point group, for certain microporous aluminosilicates are set out in Table II.

TABLE II

| Zeolite | Channel Dimensions | Symmetry Point Group | Symmetry Space Group |
|---|---|---|---|
| Bikitaite $Li_2O.Al_2O_3.4SiO_2.2H_2O$ | 3.2 × 4.9 | 2 | $P2_1$ |
| Edingtonite $BaO.Al_2O_3.3Si_2.4H_2O$ | 3.5 × 3.9 | 222 | $P2_12_12$ |
| Harmotome $BaO.Al_2O_3.6SiO_2.6H_2O$ | (4.2 × 4.4)(2.8 × 4.8)(3.3) | m | Cm |
| Cancrinite $Na_6Al_6Si_6O_{24}.CaCO_3.2H_2O$ | 6.2 | 6 | $P6_3$ |
| Heulandite $CaO.Al_2O_3$ | (4.0 × 5.5)(4.4 × 7.2)(1 × 4.7) | m | Cm |
| Laumonite $CaO.Al_2O_3.4SiO_2.4H_2O$ | 4.6 × 6.3 | m | Am |
| Scolecite $CaO.Al_2O_3.3SiO_2.3H_2O$ | 2.6 × 3.9 | m | Cc |
| Thomsonite $(Na_2Ca).O.Al_2O_3.2SiO_2.2.4H_2O$ | 2.6 × 3.9 | mm2 | Pnn2 |
| Yugawaralite $CaO.Al_2O_3.6SiO_2.4H_2O$ | 3.6 × 2.8 | m | Pc |
| Natrolite $Na_2O.Al_2O_3.3SiO_2.2H_2O$ | 2.6 × 3.9 | mm2 | Fdd2 |

Amongst the synthetic molecular sieves the aluminosilicate ZSM11, identified fully in British Patent Specification No. 1339501, is allocated to tetragonal non-enantiomorphous point group $\overline{4}2$ m (Nature 1978 Vol 275 page 119), as is its silica analogue "Silicalite-2" (Nature, Vol 280, 23 Aug. 1979 pages 664–5 and U.S. Pat. No. 4,073,865 referred to above). The aluminosilicate Theta I, identified fully in European Patent Publication No. 0057049, is allocated to space group Cmc2, which is derived from orthohombic non-enantiomorphous point group $mm^2$ (Nature, Vol 312, 6 Dec. 1984. pages 533–534). Without limiting the scope of the invention in any way thereto, the use of the zeolite ZSM11, Theta I or Silicalite 2 is therefore particularly provided according to the present invention. While naturally occurring materials are not excluded it is preferred for reasons of purity that they be synthetic. This need not limit the variety of materials available since new synthetic zeolites, and synthetic analogues of naturally occurring zeolites, are constantly being produced. The asymmetric natural zeolite edingtonite was synthesised as long ago as 1974 (Barrer et al; J. Chem. Soc. (Dalton) 1974, pages 934–41).

The channels or cavities of opposite symmetry in asymmetrical molecular sieve materials apparently show discrimination between the appropriate enantiomers of a racemate. It is thought that the distinct enantiomer may be adsorbed preferentially into those channels in an asymmetrical molecular sieve material which are appropriate to its symmetry, as shown by its optical form, leaving other channels, appropriate to the opposite optical form, to be occupied preferentially by the appropriate enantiomeric component of the racemate, the remaining enantiomeric component of the racemate being consequently less strongly adsorbed, and being separable on the basis of this difference.

While the presence of the distinct enantiomer would be expected to result in some degree of concentration of the enantiomer of opposite optical form in solution recovered from the molecular sieve material irrespective of its absorption affinity for the molecular sieve it is preferred, for optimum performance, that the distinct enantiomer be of a compound which is more strongly adsorbed thereon than the compound of the racemate. Relative adsorption affinities are readily established by simple absorption tests carried out on solutions of the compounds in question followed by analysis of the eluate.

The invention may be put into practice by various operational procedures involving contacting the racemate, in liquid form or in solution, with a bulk of the adsorbent and recovering one or more fractions of the contacted racemate, relatively concentrated or depleted in one of the enantiomers, from the adsorbent and if desired recycling the one or more fractions to enhance that concentration or depletion.

According to one procedure the asymmetric molecular sieve material is first contacted with a solution of the distinct enantiomer so that it absorbs a quantity of that enantiomer, and is separated from the residue of that solution and the molecular sieve material is then contacted with a solution of the racemate whereupon it tends to adsorb one of the enantiomeric components preferentially, and is separated from the residue of that solution and the adsorbed solution enriched in one enantiomeric component of the racemate is recovered from the molecular sieve material and may be recycled to further enrich it in the said enantiomeric component. The other enantiomeric component may be separated from the residual racemate solution and from any distinct enantiomer which may be present or may be recycled to further increase the concentration of the other enantiomeric component therein. The distinct enantiomer may also be recycled.

According to a further procedure, which is particularly adaptable to continuous or semi-continuous operation, the distinct enantiomer is included with the solution of the racemate and the molecular sieve material is contacted with the resulting mixture. It has been found that if the solution containing the distinct enantiomer and the racemate is passed through a bed of the molecular sieve material the effect of the presence of the distinct enantiomer is to retard one of the enantiomeric constituents of the racemate thereby producing an effluent having a differential concentration of the said enantiomeric constituents with time. The recovery of fractions of eluate and recycling procedures will progressively increase this differential providing the basis for a practical resolution process. Again, the distinct enantiomer can be removed from fractions rich in it by known chemical or physical separation techniques and recycled.

The selection of a distinct enantiomer and indeed the selection of a racemate for use or treatment according to this invention is preferably made on the basis of its molecular size, polarity and polarisability. It is well known that molecular sieves such as zeolites can often adsorb molecules having theoretical dimensions somewhat larger than the pore size of the molecular sieve although said average dimension is preferably not more than 3 Angstroms particularly preferably not more than 2 Angstroms and, for example, very suitably not more than 1 Angstrom greater than the greatest pore diameter and the selection of the distinct enantiomer and of the racemate is preferably made on this basis. Molecules which are substantially smaller than the said pores may tend to pass through the molecular sieve without attaining a sufficiently intimate relationship with the internal structure of the molecular sieve to give a sufficiently marked resolution effect. Preferably the distinct enantiomer and the racemate have an average molecular dimension at least equal to one third, particularly preferably to one half for example very suitably to three quarters of the minimum pore diameter. The pore diameter of particular molecular sieves is well known. For example, that of zeolite ZSM11 and of its silica analogue Silicalite II is in the approximate range 5.3–6.3 Angstroms. Preferably the enantiomer is such that it passes through the said material but less readily than the racemate. It may be that different molecular sieve materials, particularly the synthetic molecular sieve materials preferred in the practice of this invention will, apart from the effect of pore size, have different affinities for the same compound so that trials with the molecular sieve material of choice may be advantageous to determine the particular enantiomer to be used or the molecular sieve to be used to treat a particular racemate. This is well within the ordinary skill in the art relating to molecular sieve usage. Such a selection technique will enable the invention to be applied to new molecular sieve materials having asymmetry, or known molecular sieve materials which are found to have asymmetry.

If the molecular sieve material is itself enantiomeric the use of a distinct enantiomer may be unnecessary and, according to the invention, the solution of the racemate may merely be passed through a bed of the molecular sieve material or otherwise contacted with it, to achieve resolution.

The distinct enantiomer may be selected from enantiomers of any suitably sized compounds having optical activity. Very suitably the enantiomer may be an amine for example a suitable amino acid such as proline, or a suitable heterocyclic nitrogen-containing compound such as a piperidine or a quaternary ammonium salt thereof, for example 3-methyl piperidine or 3-methyl N.N. dimethyl piperidinium bromide or a suitable alicyclic compound for example alpha pinene or a suitable aliphatic alcohol for example 2-methyl butanol. Preferably, the distinct enantiomer is selected from suitable cobalt complexes, particularly preferably complexes with relatively small organic ligands containing, for example, not more than 4 carbon atoms. Preferably the organic ligand may be an amine. One example of a suitable cobalt+3 complex is the bis(ethylene diamine) complex.

The solutions of the racemate or of an enantiomer referred to above are preferably in an organic solvent. The organic solvent preferably includes a polar solvent in at least 5% particularly preferably at least 25% by volume in a non-polar solvent or consists of a polar solvent. An example of a suitable polar solvent is methanol and an example of a suitable non-polar solvent is hexane.

While the present invention may be applicable to the production of directly biochemically useful enantiomers, if such may be adsorbed within a given asymmetrical molecular sieve, its main utility may be in the production of relatively small enantiomer molecules which are therefore more suited to adsorption within the normal channel size range of from about 3 to 15 Angstroms, of known zeolite molecular sieves.

A current approach to the production of enantiomeric biochemically useful materials is the "chiron" approach whereby the synthesis is based on the use of small highly functional chiral "synthons" such as, for example, 1-phenyl-ethanol, epichlorhydrin, methyl p-toluene sulphoxide, 4-bromo 1,2-epoxy butane, propylene oxide, 2-chlorobutane and 2-aminobutane. The synthesis of even these simple molecules in enantiomeric form is time-consuming and laborious and the provision of the present process for the adsorptive resolution of the racemates is potentially of great benefit.

The present invention will now be illustrated by reference to the following Examples. Examples 1–3, 5 and 8 are according to the invention. Example 4, 6, 7 and 9 are inserted for comparative purposes only.

EXAMPLES 1–3

Resolution of (+/−)-1-phenylethanol racemate.

The proportion of (+) and (−) enantiomers in a 1-pheylethanol racemate was measured before and after being treated according to the invention, by high pressure liquid chromatography on a BAKERBOND DNBPG (Trademark) chiral column of J. T. Baker Research Products. The stationary phase was an enantiomer of N-3,5-dinitrobenzoyl-phenylglycine bonded covalently to a 5-micron aminopropyl silica. The mobile phase was 99.5% n-hexane and 0.5% isopropyl alcohol. Detection was by UV absorbance at 254 nm.

A 5 g sample of zeolite ZSM11, produced according to U.S. Pat. No. 3,832,449 was immersed in 25 ml of a 1% by volume solution of (+)—phenylethylamine in n-hexane allowed to stand overnight, removed, filtered and air dried. The sample of zeolite was then immersed in 25 ml of a 1% by volume solution of the 1-phenylethanol racemate in 99.5% by volume n-hexane and 0.5% by volume toluene. Over a period of 7 hours samples of the racemate were removed periodically and the ratio of each enantiomer to toluene determined by high pressure liquid chromatography using the method as above. Over the 7 hour period the proportion of one enantiomer in the samples dropped by 3.7% and the other by 6.6%.

Further tests were carried out on the resolution of (+/−)-1-phenyl ethanol using ZSM11 molecular sieve loaded with (−)-2-methyl butanol (Example 2) or (+)-alpha pinene (Example 3). In both Examples a clear alteration of the proportion of the enantiomers of the 1-phenyl ethanol was obtained compared with no alteration when the 1-phenyl ethanol was passed through unloaded zeolite ZSM11.

EXAMPLE 4

Example 1 was repeated using the symmetrical zeolite ZSM5 produced according to U.S. Pat. No.

3,702,886. No change in the ratio of enantiomers in the racemate was detected.

EXAMPLE 5

Resolution of methyl phenyl sulphoxide racemate.

The proportion of (+) and (−) enantiomers in a methyl phenyl sulphoxide racemate was measured before and after being treated according to the invention by gas chromatography on a 25 m CHIRASIL-VAL (Trademark) chiral capilliary column supplied by Applied Science. The stationary phase was an enantiomer of valine-t-butylamide coupled to a dimethylsiloxane/carboxyalkylmethylsiloxane copolymer.

A stainless steel column 30 cms long and 0.6 cm outside diameter was packed with the zeolite ZSM11. A solvent mixture consisting of a volume ratio of 45 n-hexane, 35 methanol and 10 isopropyl alcohol was pumped through the column at a rate of 1 ml per minute. 10 microliters of a dilute solution of methyl phenyl sulphoxide racemate in the same solvent was introduced into the solvent and was found to elute without any alteration in the ratio of its enantiomers. The solvent mixture being pumped through the column was then adjusted in composition to a volume ratio of 45 n-hexane, 44 methanol, 11 isopropyl alcohol with 0.5 g of a proline enantiomer. The same quantity of methyl phenyl sulphoxide racemate as used above was added to the adjusted solution. Based on peak areas the ratio of the enantiomers of methyl phenyl sulphoxide in the eluate was found to alter with time from 48.5:51.5 through 47.6:52.4 to 44.4:55.6.

EXAMPLES 6 TO 9

The equipment was set up with four small stoppered vessels. Two (Examples 4 and 5) contained a natural calcium montmorillonite clay having a cation exchange capacity of 76 m eq/100 g (available from Laporte Industries Limited as "Surrey Powder") (2 g) and two contained synthetic zeolite ZSM11 (1 g) (Examples 6 and 7). The bulk density of the montmorillonite was greater than that of the ZSM11 and the different weights compensated for this.

5 ml of a solution containing 103 micro-moles (+)-bis(ethylenediamine)cobalt(III) bromide demineralised water were added to one of the montmorillonite samples (Example 4) and one of the ZSM11 samples (Example 6). 5 ml of demineralised water was added to the other two samples.

Each of the four samples was then treated with 5 cm$_3$ of a solution containing 165 micro-moles of methyl phenyl sulphoxide in methanol.

The four samples were then left to stand for two days, with occasional shaking, to equilibrate. The supernatant liquids were then drawn off and analysed to give the results in Table III. Analysis was by capillary gas chromatography using a 25 m 'Chirasil-Val' column. The gas chromatography conditions were as follows:
Injector 120° C.
Detector 140° C.
Initial oven temperature 80° C. for 1 minute, then linear temperature programmed to 120° C. at 40° C. per minute. The two enantiomers elute after 10.2 and 10.5 minutes.

TABLE III

| Example | (+)- METHYL PHENYL SULPHOXIDE AMOUNT SORBED/micro-moles | (−) METHYL PHENYL SULPHOXIDE AMOUNT SORBED/micro-moles | RATIO (+)/(−) |
|---|---|---|---|
| 6 | 19.3 | 28.8 | 1.49 |
| 7 | 53.8 | 55.5 | 1.03 |
| 8 | 17.4 | 40.8 | 2.34 |
| 9 | 45.7 | 45.6 | 1.00 |
| STANDARD SOLUTION OF METHYL PHENYL SULPHOXIDE | 82.5 | 82.5 | 1.00 |

The data in Table III shows that the use of the molecular sieve material according to the invention (Example 8) gives a considerably more effective resolution than the layered clay mineral material (Example 6).

We claim:

1. A process for the resolution of a racemate of a compound by stereoselective adsorption on a solid adsorbent characterised by the use of a crystalline molecular sieve material having an asymmetrical crystal structure as the adsorbent.

2. A process as claimed in claim 1 wherein the racemate in liquid form or as a solution is contacted with a bulk of the adsorbent and one or more fractions of the so contacted racemate relatively concentrated or depleted in one of the enantiomers thereof, are recovered from the adsorbent.

3. A process as claimed in claim 2 wherein said one or more fractions are recycled to further contact with the bulk of adsorbent thereby to enhance said depletion or concentration.

4. A process as claimed in claim 1 wherein the racemate is in the form of a solution comprising a polar organic solvent.

5. A process as claimed in claim 1 wherein the adsorbent is in contact with a distinct enantiomer of a compound separable from that of the racemate.

6. A process as claimed in claim 5 further characterised in that the molecular sieve material is first contacted with a solution of the distinct enantiomer and is separated from the residue of that solution and is then contacted with the solution of the racemate and is separated from the residue of that solution, and adsorbed solution, containing an increased proportion of one enantiomeric constituent of the racemate, is recovered from the molecular sieve material.

7. A process as claimed in claim 5 further characterised in that the molecular sieve material is contacted with a solution of racemate compound and of the distinct enantiomer.

8. A process as claimed in claim 7 wherein the solution is passed through a body of the molecular sieve material and separate fractions of an eluate containing differing ratios of the enantiomeric constituents of the racemate and of the distinct enantiomer therefrom are recovered therefrom.

9. A process as claimed in claim 8 wherein the distinct enantiomer is recovered from at least some of the fractions and recycled.

10. A process as claimed in claim 8 wherein fractions containing an increased proportion of one enantiomeric constituent of the racemate, relative to the other, are recycled to further increase said proportion.

11. A process as claimed in claim 1 wherein the crystalline molecular sieve material having an asymmetrical crystal structure comprises a three dimensional silica framework.

12. A process as claimed in claim 11 wherein the molecular sieve material is a zeolite.

13. A process as claimed in claim 12 wherein the zeolite is ZSM11, Silicalite 2, or Theta I.

14. A process as claimed in claim 1 wherein the compound is proline or phenylethylamine.

15. A process as claimed in claim 1 wherein the distinct enantiomer is an enantiomer of a cobalt complex.

16. A process as claimed in claim 15 wherein the ligand forming the complex is an amine containing not more than 4 carbon atoms.

17. A process as claimed in claim 1 for the resolution of a racemate of an alkyl aryl sulphoxide.

18. A process as claimed in claim 17 wherein the sulphoxide is a 1 to 4 carbon alkyl substituted, or a 6 carbon cycloalkyl substituted phenyl sulphoxide.

19. The process of claim 1 wherein the molecular sieve material is selected from the group consisting of aluminosilicate, aluminophosphate and silica molecular sieves.

20. The process of claim 1 wherein the molecular sieve material has an average pore diameter within the range of from 2 to 20 Angstroms.

21. The process of claim 1 wherein the racemate is in vapor form.

* * * * *